United States Patent [19]

Ohrui et al.

[11] 4,199,410
[45] Apr. 22, 1980

[54] PURIFICATION OF CRUDE ACRYLIC ACID

[75] Inventors: Tetsuya Ohrui; Michio Kato, both of Niihama; Masami Ayano, Saijo; Tsunejiro Kawaguchi; Tadashi Abe, both of Niihama, all of Japan

[73] Assignee: Sumitomo Chemical Company, Limited, Osaka, Japan

[21] Appl. No.: 929,696

[22] Filed: Jul. 31, 1978

[30] Foreign Application Priority Data

Aug. 4, 1977 [JP] Japan ................................ 52-93789

[51] Int. Cl.² ...................... B01D 3/34; C07C 51/44; C07C 57/04
[52] U.S. Cl. ........................................ 203/49; 203/73; 203/DIG. 21; 562/600
[58] Field of Search ................... 203/49, 73, DIG. 21, 203/99, DIG. 19; 562/600

[56] References Cited

U.S. PATENT DOCUMENTS

| | | | |
|---|---|---|---|
| 3,406,100 | 10/1968 | Karafian | 203/99 |
| 3,513,632 | 5/1970 | Hess et al. | 562/600 |
| 3,781,193 | 12/1973 | Sennewald et al. | 562/600 |
| 3,859,175 | 1/1975 | Ohrui et al. | 562/600 |
| 3,932,500 | 1/1976 | Duembgen et al. | 562/600 |

Primary Examiner—Wilbur L. Bascomb, Jr.
Attorney, Agent, or Firm—Stevens, Davis, Miller & Mosher

[57] ABSTRACT

A process for purifying crude acrylic acid characterized in that high-purity purified acrylic acid containing little or no low boiling aldehydes is obtained by rectifying a crude acrylic acid consisting essentially of acrylic acid and containing low boiling substances such as acetaldehyde, acrolein, water and acetic acid and/or high boiling substances such as maleic acid, phenol, benzaldehyde and acrylic acid dimer, thereby removing said low boiling substances and then high boiling ones, and then stripping trace amounts of remaining low boiling aldehydes with an inert gas such as nitrogen or air at a liquid to gas molar ratio of 2 to 20.

9 Claims, 1 Drawing Figure

FIGURE
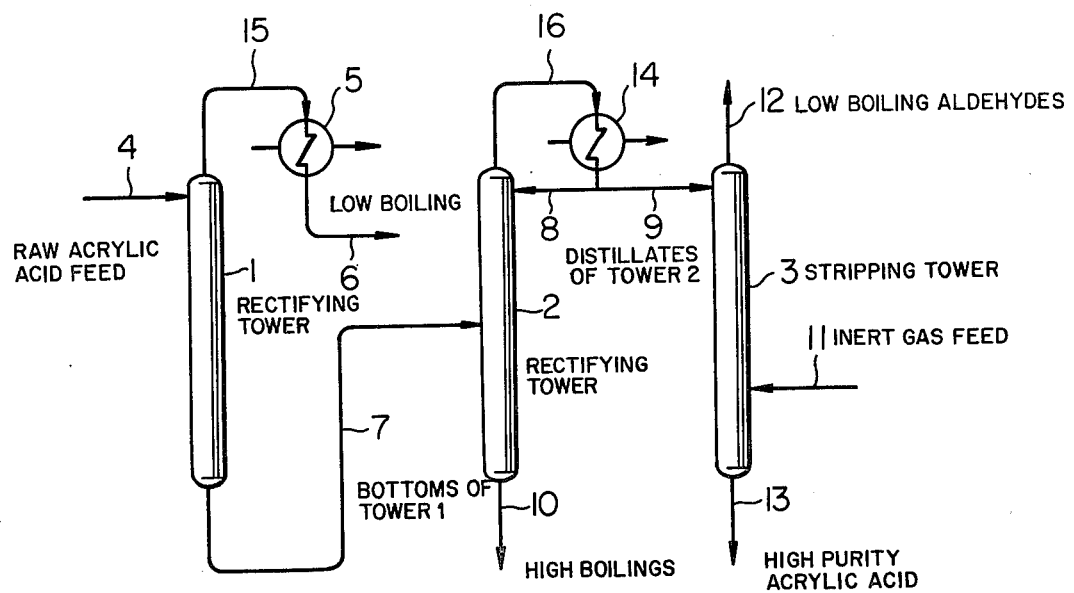

PURIFICATION OF CRUDE ACRYLIC ACID

The present invention relates to a purification process for obtaining high-purity acrylic acid from mixtures consisting essentially of acrylic acid. More particularly, it relates to a process for producing high-purity purified acrylic acid containing little or no low boiling aldehydes which comprises rectifying a crude acrylic acid containing substances having a lower boiling point than that of acrylic acid (e.g. acetaldehyde, acrolein, water, acetic acid) and/or substances having a higher boiling point than that of acrylic acid (e.g. maleic acid, phenol, benzaldehyde, fumaric acid, phthalic acid, acrylic acid dimer) as impurities thereby separating said low boiling and high boiling substances from the crude acrylic acid, and then stripping trace amounts of remaining low boiling aldehydes, particularly acrolein, with an inert gas such as nitrogen or air.

By polymerizing high-purity purified acrylic acid into high polymers having a molecular weight of more than several ten millions, followed by neutralizing if necessary, there are obtained polyacrylic acids or sodium polyacrylates which are used as flocculants, paper additives, adhesives, materials for ABS resin preparation and the like. For these uses, it is necessary to raise the degree of polymerization to a molecular weight of more than several ten millions in the course of polymerization. In some cases, however, the increase of the degree of polymerization to the required molecular weight is often difficult, on account of the adverse effect of trace amounts of impurities in the raw acrylic acid. Particularly, low boiling aldehydes such as acrolein have a strong action to inhibit polymerization of acrylic acid, and, as is well known, the polymerization is strikingly inhibited by said aldehydes of only several ten ppm in a raw acrylic acid.

Hitherto, acrylic acid has been produced by the Reppe process or hydrolysis of acrylonitrile. Recently, however, production of acrylic acid by direct oxidation of propylene was developed, and this process is mainly employed at present. Since, however, various kinds of low boiling or high boiling aldehydes are produced as by-products in the course of the oxidation of propylene, the crude acrylic acid produced by this process contains, even though purified, various kinds of aldehydes of considerably high concentration as compared with the purified acrylic acid resulting from the aforesaid two conventional processes, particularly hydrolysis of acrylonitrile. Consequently, the purified acrylic acid resulting from oxidation of propylene is generally inferior to the purified acrylic acid prepared by the hydrolysis of acrylonitrile in polymerization performances, and the latter purified acrylic acid has been mainly used as a material for high polymerization.

These low boiling aldehydes may be considered as easily separable by the conventional rectification processes, since they have sufficiently a large relative volatility as compared with acrylic acid. The rectification carried out by the inventors, however, showed that removing said aldehydes to less than 100 ppm by rectification alone was very difficult. The content of said low boiling aldehydes in acrylic acid for high polymerization is generally less than 10 ppm, preferably less than 5 ppm. Consequently, the inventors could not help giving up the production of purified acrylic acid for high polymerization by mere rectification of the crude acrylic acid resulting from the direct oxidation of propylene.

The inventors extensively studied the reason why removal of trace amounts of said low boiling aldehydes by rectification is difficult. As a result, the following was found: The low boiling aldehydes such as acrolein are little in amounts, but they are easily dimerized or hydrated in the presence of water, thereby forming dimers or hydrates; these dimers or hydrates act as a high boiling substance on acrylic acid and remain as a bottom liquor during separation of low boiling substances such as the low boiling aldehydes, water and acetic acid by rectification; these remaining dimers or hydrates of the low boiling aldehydes decompose and regenerate said low boiling aldehydes during the subsequent separation of high boiling substances by rectification or during storage; and the regenerated aldehydes enter the purified acrylic acid as a final product, and therefore their content in the acrylic acid can not be reduced to less than 100 ppm by rectification alone. In order to overcome these difficulties, the inventors extensively studied how to remove trace amounts of these low boiling aldehydes such as acrolein from the rectified acrylic acid. As a result, the inventors succeeded in removing the remaining low boiling aldehydes to less than 10 ppm, preferably less than 5 ppm, by removing low boiling substances and then high boiling substances from the crude acrylic acid and then stripping trace amounts of said low boiling aldehydes entering the purified acrylic acid after being regenerated by decomposition of dimers and hydrates thereof, using an inert gas such as nitrogen or air.

That is, the present invention provides a process for purifying a crude acrylic acid which comprises producing high-purity purified acrylic acid containing little or no low boiling aldehydes by rectifying the crude acrylic acid consisting essentially of acrylic acid and containing low boiling substances (e.g. acetaldehyde, acrolein, water, acetic acid) and/or high boiling substances (e.g. maleic acid, phenol, benzaldehyde, acrylic acid dimer), thereby removing said low boiling substances and then high boiling ones, and then stripping trace amounts of the remaining low boiling aldehydes using an inert gas such as nitrogen or air.

Figure shows one example for carrying out the purification of crude acrylic acid according to the present invention. In the drawing, 1 is a rectifying tower for separation of low boiling substances, 2 is a rectifying tower for separation of high boiling substances, 3 is a stripping tower for removal of low boiling aldehydes, 5 and 14 are condensers, and 4, 6, 7, 8, 9, 10, 11, 12, 13, 15 and 16 are liquid or gas lines.

The crude acrylic acid used in the present invention is one which is obtained by the direct oxidation of propylene, and it contains low boiling compounds (e.g. acetaldehyde, acrolein, water, acetic acid) and/or high boiling compounds (e.g. maleic acid, phenol, benzaldehyde, acrylic acid dimer) as impurities. The content of these impurities is not constant since it varies with the condition of oxidation of propylene. But, the present invention is not affected by the variation of the content of the impurities.

Separation of the low boiling substances and/or high boiling substances by rectification is satisfactorily carried out by separating firstly the former substances and then the latter ones. The separation may be carried out by means of any form of rectifying tower and in any form of operation. For example, the rectifying tower may be one in which the substances can be withdrawn as a side cut, or composite towers comprising a plural number of rectifying towers, and the operation may be carried out in a continuous form or batchwise form.

The operating pressure in the rectifying tower is less than 400 mmHg, preferably less than 100 mmHg, and in this case combined use of a suitable polymerization inhibitor is of course necessary since acrylic acid to be treated is a substance having a property to violently polymerize by heat.

Both the low boiling fraction and high boiling residue produced as by-products in the distillation contain a considerable amount of acrylic acid, and therefore they can be used as a material for production of acrylic acid esters such as methyl acrylate.

The acrylic acid fraction obtained by distillation is subjected to stripping with an inert gas such as nitrogen or air for removal of the low boiling aldehydes. The stripping is carried out at 15° to 80° C., preferably 20° to 50° C. The stripping temperature of less than 15° C. is not desirable economically, since the vapor pressure of the low boiling aldehydes becomes so low that the rate of stripping is low. The temperature of higher than 80° C. is not also desirable, since the rate of polymerization of acrylic acid becomes high.

The amount of the inert gas used for stripping the low boiling aldehydes is properly determined from the economical viewpoint of the stripping tower. Because, as the amount increases, the tower height necessary to obtain a required rate of stripping becomes small, but on the contrary the tower diameter becomes large. Too large amounts of the inert gas are however disadvantageous, since the amount of acrylic acid accompanying the inert gas, i.e. the loss of the acid, becomes large. Accordingly, it is desirable that the molar ratio of liquid to gas in the stripping tower is selected within the range of about 2 to about 20.

The purification of crude acrylic acid according to the present invention is characterized in that the crude acrylic acid is first subjected to rectification and then to stripping with an inert gas for removal of low boiling aldehydes entering the acrylic acid fraction. But, the removal of the low boiling aldehydes regenerated by decomposition can be achieved not only by the stripping with inert gas, but also by repetition of rectification. But, the purification process including the latter method, that is, a process comprising separation of low boiling substances and then high boiling ones by rectification and separation of the regenerated low boiling aldehydes by re-rectification, is not advantageous as an industrial process, considering that it is uneconomical thermally and that acrylic acid is a substance which is easily polymerized or dimerized by the action of heat.

The present invention will be illustrated in more detail with reference to the accompanying drawing. FIG. 1 shows one embodiment of the present invention, but the present invention is not limited thereto.

A tower 1 is a rectifying tower for separation of low boiling substances, a tower 2 is a rectifying tower for separation of high boiling substances and a tower 3 is a stripping tower for removal of low boiling aldehydes. A raw acrylic acid is supplied to the top of the tower 1 through a line 4. A top vapor is passed through a line 15, condensed in a condenser 5 and withdrawn from a line 6 as the distillate of low boiling substances. A bottom liquor in the tower 1 is supplied to the middle portion of the tower 2 through a line 7. A top vapor in the tower 2 is passed through a line 16, condensed in a condenser 14 and circulated to the tower 2 through a line 8. A rectified acrylic acid freed from low boiling substances and high boiling ones is obtained through a line 9. This rectified acrylic acid contains less than 100 ppm of low boiling aldehydes, for example acrolein, regenerated by decomposition of dimers and hydrates thereof, and therefore it is supplied to the top of the stripping tower 3 through a line 9. A bottom liquor in the tower 2 contains high boiling substances and is withdrawn through a line 10. An inert gas such as nitrogen or air is supplied to the tower 3 through a bottom line 11. Said low boiling aldehydes are removed from the rectified acrylic acid by stripping and discharged through a top line 12. A high-purity purified acrylic acid from which the low boiling aldehydes are removed to less than 10 ppm is obtained from the bottom of the tower 3 through a line 13.

Next, the present invention will be illustrated in more detail with reference to the following example and comparative example, but it is not intended to limit the present invention to this example.

EXAMPLE

Purification of crude acrylic acid was carried out according to the same flow sheet as in Figure except that the line 7 was connected not to the middle portion but to the bottom of the rectifying tower 2. Each tower was operated according to the conditions described in Table 1, and as a result the composition and flow amount at every portion of the flow sheet in Figure were as shown in Table 2. The amount of nitrogen supplied through a line 11 was 50 cc/hr.

Table 1

|  | Unit | Rectifying tower 1 | Rectifying tower 2 | Stripping tower 3 |
| --- | --- | --- | --- | --- |
| Material of tower | — | Hard glass | Hard glass | Hard glass |
| Diameter of tower | mm | 30 | 30 | 15 |
| Packing | mm | 3 in diameter Dixon packing | 3 in diameter Dixon packing | 3 in diameter Dixon packing |
| Height of packing section | mm | 700 | 700 | 1000 |
| Operating pressure | mmHg | 25 | 25 | 760 |
| Bottom temperature | °C. | 59 | 60 | 25 |
| Reflux ratio | — | — | 5.0 | — |

Table 2

|  | Unit | Line-4 | Line-6 | Line-7 | Line-9 | Line-10 | Line-13 |
| --- | --- | --- | --- | --- | --- | --- | --- |
| Flow amount | g/hr | 400 | 180 | 220 | 119.9 | 100.1 | 119.5 |
| Acrylic Acid | wt. % | 94.0 | 91.1 | 96.4 | 98.9 | 93.4 | 99.0 |
| Water content | wt. % | 1.72 | 3.49 | 0.27 | 0.42 | 0.09 | 0.40 |
| Acrylic acid dimer | wt. % | 2.8 | 3.3 | 2.4 | 0.43 | 4.76 | 0.45 |
| Acrolein | ppm | 150 | 295 | 31 | 45 | 14 | 2 |
| Other low boiling substances | ppm | 200 | 3460 | 80 | 130 | 20 | 4 |

Table 2-continued

|  | Unit | Line-4 | Line-6 | Line-7 | Line-9 | Line-10 | Line-13 |
| --- | --- | --- | --- | --- | --- | --- | --- |
| Benzaldehyde | ppm | 670 | 370 | 910 | 10 | 1980 | 10 |

COMPARATIVE EXAMPLE

The flow sheet in Figure was changed as follows: The arrangement of the rectifying towers 1 and 2 and stripping tower 3 was changed in order of rectifying tower 1, stripping tower 3 and rectifying tower 2; the line 7 was connected to the top of the stripping tower 3; and the line 13 was connected to the bottom of the rectifying tower 2 whereby purified acrylic acid was withdrawn from the line 9.

The operating conditions in the stripping tower 3 were changed as follows: The amount of nitrogen blown into the bottom of the tower 3 was increased to 100 cc/hr; and the operating temperature in the tower 3 was adjusted to agree with the bottom temperature, 60° C., of the rectifying tower 1.

The operating conditions in the rectifying towers 1 and 2, and the flow amount and composition of the raw acrylic acid supplied through the line 4 were completely the same as in Example.

Purification was carried out according to the flow sheet and operation conditions as described above. As a result, it was found that the purified acrylic acid withdrawn from the top of the rectifying tower 2 through the line 9 contained acrolein of as much as 35 ppm.

What is claimed is:

1. A process for purifying crude acrylic acid comprising the steps of
   (1) rectifying a crude acrylic acid consisting essentially of acrylic acid and low boiling impurities including acrolein (a) to remove initially a major portion of said low boiling impurities and then (b) to remove high boiling impurities either present in said crude acrylic acid or the high boiling impurities formed during the initial rectification, and then
   (2) removing by stripping trace amounts of acrolein and other low boiling impurities with an inert gas at a liquid to gas molar ratio of about 2 to about 20, thereby forming a high purity acrylic acid containing acrolein and other low boiling impurities in a total quantity less than 100 ppm.
2. The process of claim 1 wherein said inert gas is selected from the group consisting of nitrogen and air.
3. The process of claim 1 wherein said crude acrylic acid is formed by the oxidation of propylene.
4. The process of claim 1 wherein said high purity acrylic acid contains acrolein and other low boiling impurities in a total quantity less than 10 ppm.
5. The process of claim 1 wherein said high purity acrylic acid contains acrolein and other low boiling impurities in a total quantity less than 5 ppm.
6. A process according to claim 1, wherein the operating pressure during rectification is less than 400 mmHg.
7. The process of claim 6 wherein the operating pressure during rectification is less than 100 mmHg.
8. A process according to claim 1, wherein the stripping temperature of the low boiling impurities is 15°–80° C.
9. The process of claim 8 wherein the stripping temperature of the low boiling impurities is 20° to 50° C.

* * * * *